(12) United States Patent
Gho et al.

(10) Patent No.: US 9,220,763 B2
(45) Date of Patent: Dec. 29, 2015

(54) NANO-VEHICLE DERIVED FROM TUMOR TISSUE, AND CANCER VACCINE USING SAME

(75) Inventors: Yong Song Gho, Pohang-si (KR); Yoon Keun Kim, Pohang-si (KR); Eun Yeong Lee, Pohang-si (KR); Su Chul Jang, Gyeongsangbuk-do (KR)

(73) Assignee: POSTECH ACADEMY-INDUSTRY FOUNDATION, Pohang-si, Gyeongsangbuk-do (KR)

( * ) Notice: Subject to any disclaimer, the term of this patent is extended or adjusted under 35 U.S.C. 154(b) by 102 days.

(21) Appl. No.: 13/823,315

(22) PCT Filed: May 25, 2012

(86) PCT No.: PCT/KR2012/004162
§ 371 (c)(1),
(2), (4) Date: Mar. 14, 2013

(87) PCT Pub. No.: WO2012/165815
PCT Pub. Date: Dec. 6, 2012

(65) Prior Publication Data
US 2013/0177595 A1    Jul. 11, 2013

(30) Foreign Application Priority Data
May 27, 2011  (KR) .................. 10-2011-0050854

(51) Int. Cl.
| | |
|---|---|
| *A61K 9/133* | (2006.01) |
| *A61K 47/00* | (2006.01) |
| *A61K 47/36* | (2006.01) |
| *A61K 47/40* | (2006.01) |
| *A61K 39/00* | (2006.01) |
| *A61K 9/127* | (2006.01) |
| *A61K 47/10* | (2006.01) |
| *A61K 38/17* | (2006.01) |

(52) U.S. Cl.
CPC ............. *A61K 39/0011* (2013.01); *A61K 9/127* (2013.01); *A61K 47/10* (2013.01); *A61K 47/40* (2013.01); *A61K 38/1709* (2013.01); *A61K 2039/55561* (2013.01)

(58) Field of Classification Search
None
See application file for complete search history.

(56) References Cited

U.S. PATENT DOCUMENTS

| | | |
|---|---|---|
| 2002/0039571 A1 | 4/2002 | Falkenberg et al. |
| 2003/0022854 A1 | 1/2003 | Dow et al. |
| 2010/0075315 A1 | 3/2010 | Pietrzkowski |
| 2011/0123620 A1 | 5/2011 | Weigandt et al. |
| 2013/0115241 A1 | 5/2013 | Gho et al. |

FOREIGN PATENT DOCUMENTS

| | | |
|---|---|---|
| EP | 2589377 A2 | 5/2013 |
| JP | 2003-535017 A | 11/2003 |
| JP | 2005-281266 A | 10/2005 |
| JP | 2009-534309 A | 9/2009 |
| WO | WO 99/58645 A1 | 11/1999 |
| WO | WO 2009/146523 A1 | 12/2009 |
| WO | WO 2011/031298 A1 | 3/2011 |
| WO | WO2012/002759 | * 1/2012 |

OTHER PUBLICATIONS

Dai et al (Journal of Molecular Therapy, 2008, vol. 16, pp. 782-790).*
Chaput et al (Journal of Immunology, 2004, vol. 172, pp. 2137-2146).*
Xiu et al (Journal of Molecular Medicine, 2007, vol. 85, pp. 511-521).*
J.J. Bergers, et al., "Vesicles for tumour-associated antigen presentation to induce protective immunity: preparation, characterization and enhancement of the immune response by immunomodulators", Journal of Controlled Release, 29 (1994) 317-327.
T. Chen, et al., "Chemokine-Containing Exosomes Are Released from Heat-Stressed Tumor Cells via Lipid Raft-Dependent Pathway and Act as Efficient Tumor Vaccine", The Journal of Immunology, 2011, 186: 2219-2228.
Japanese Office Action dated May 27, 2014 for Japanese Patent Application No. 2013-534840.
Y. Xie, et al; Membrane-bound HSP70-engineered myeloma cell-derived exosomes . . . ; Journ. Cell. Mol. Med.; vol. 14; No. 11; Nov. 2010; pp. 2655-2666.
W. Chen, et al; Efficient induction of antitumor T cell immunity by exosomes derived from . . . ; Eur. Journ. Immunol.; vol. 36; No. 6; Jun. 2006; pp. 1598-1607.
J.A Cho, et al; Exosomes: a new delivery system for tumor antigens in cancer . . . ; Int. Journ. Cancer; vol. 114; No. 4; Apr. 2005; pp. 613-622.
E.Y. Lee, et al; Therapeutic effects of autologous tumor-derived nanovesicles on melanoma . . . ; Plos One; vol. 7; No. 3; Mar. 2012; e33330; 7 pages.

(Continued)

*Primary Examiner* — Karen Canella
(74) *Attorney, Agent, or Firm* — Lucas & Mercanti, LLP

(57) ABSTRACT

The present invention relates to a cancer vaccine, and specifically, to a pharmaceutical composition for treating cancer containing a nano-vehicle derived from tumor tissue, and a method for treating cancer using the nano-vehicle derived from tumor tissue, and the like. According to the present invention, a nano-vehicle antigen derived from tumor tissue indicates a high yield while having properties similar to those of an exocellular vehicle, and can be variously modified, and is thus expected to be very useful for developing the cancer vaccine.

19 Claims, 16 Drawing Sheets

(56) References Cited

OTHER PUBLICATIONS

A. Tan, et al; The application of exosomes as a nanoscale cancer vaccine; Int. Journ. Nanomedicine; vol. 5; Jan. 2010; pp. 889-900.
Extended European Search Report dated Feb. 19, 2014.
X. Li et al., "Nanovesicular vaccines: exosomes", Archivum Immunologiae et Therapiae Experimantalis, vol. 53, pp. 329-335, 2005, Summary and p. 333.
M. Wysoczynski et al., "Lung cancer secreted microvesicles: Underappreciated modulators of microenvironment in expanding tumors", International Journal of Cancer, vol. 125, No. 7, pp. 1595-1603, Oct. 1, 2009.
M. Szajnik et al., "Tumor-derived microvesicles induce, expand and up-regulate biological activities of human regulatory T-cells (Treg)", Plos One, vol. 5, Issue 7, pp. 1-13, Jul. 2010.
M. Baj-Krzyworzeka et al., "Tumor-derived microvesicles carry several surface determinants and mRNA of tumor cells and transfer some of these determinants to monocytes", Cancer Immunology, Immunotherapy, vol. 55, pp. 808-818, 2006.
K. Al-Nedawi et al., "Microvesicles", Cell Cycle, vol. 8, No. 13, pp. 2014-2018, Jul. 1, 2009.
R. Valenti et al., "Tumor-released microvesicles as vehicles of immunosuppression", Cancer Research, vol. 67, No. 7, pp. 2912-2915, Apr. 1, 2007.

\* cited by examiner

NANO-VEHICLE DERIVED FROM TUMOR TISSUE, AND CANCER VACCINE USING SAME

CROSS-REFERENCE TO RELATED APPLICATIONS

This application is a 371 of PCT/KR2012/004162 filed on May 25, 2012, which claims the benefit of Korean Patent Application No. 10-2011-0050854 filed on May 27, 2011, the contents of each of which are incorporated herein by reference.

TECHNICAL FIELD

The present invention relates to a cancer vaccine. More particularly, the present invention relates to a pharmaceutical composition for the treatment of cancer, comprising nanovesicles derived from a tumor tissue, and a method for treating cancer using the tumor tissue-derived nanovesicles.

BACKGROUND ART

Cancer is a broad group of various diseases, all involving unregulated cell growth without mortality, as a result of the abnormal differentiation or proliferation induced by the modification of the structural and functional unit cells. In cancer, cells invade nearby parts of the body, and may also spread to more distant parts of the body through the lymphatic system or bloodstream, and finally metastasize to other organs such as the lung, and the liver. There are over 100 different known cancers that afflict humans. Representative among them are lung cancer, colorectal cancer, stomach cancer, and liver cancer. As a rule, the risk of developing cancer generally increases with age, and there is an upward tendency in the onset of cancer worldwide since the average life of man's life has been increased. However, an effective cure for cancer has not yet been found, and thus, there is a pressing need for novel cancer treatments. Cancer is usually treated with surgery, chemotherapy, and radiation therapy. These treatments, however, may provoke significant side effects including the onset of secondary cancer, the metastasis of cancer, immune suppression, and aberrant cellular metabolisms. In consideration of problems with conventional cancer treatments, taking advantage of the immune system of patients is an idea drawing intensive attention as a potential strategy for the development of cancer therapies. The development of cancer vaccines is one of the most desirable medical approaches.

Designed to evoke potent immune responses to cancer, a cancer vaccine activates the immune mechanism of patients so as to enhance resistance to cancer. Cancer vaccination is advantageous in that it causes few side effects and it helps the immune system of patients to fight the cancer that remains even after surgery, as well as metastasized, invisible cancer, by itself. When account is taken of the fact that most cancers are generated by the modification of autologous cells, it is important for successful cancer vaccine development to select proper cancer antigens that induce the immune system of a patient to recognize cancer as an attack target. For use as a cancer antigen, a peptide or a protein that is already known to act as an antigen may be separated from cancer cells, or cancer cells themselves may be applied after treatment with radiation. These cancer antigens may be used in combination with an adjuvant or loaded to dendritic cells in order to enhance immune reactions. It is easy to prepare peptide or protein antigens if they are already known, but they may cause immune tolerance, because proper antigens differ from one patient to another. Cancer is considerably heterogeneous, and cancer-specific antigens are difficult to define. In addition, patients are different from each other in terms of cancer etiology and immunity control mechanism. Accordingly, a standardized treatment cannot guarantee success in the therapy of cancer. If obtained by surgery, a tumor tissue from a cancer patient may be used as a source of various cancer antigens specific for the patient. The use of cancer cells themselves, however, may evoke side effects including the risk of oncogenesis and autoimmune responses. There is therefore a need for a tumor-derived cancer vaccine that is of high utility and safety.

Nano-sized vesicles may be used as an antigen in cancer vaccination. Nano-sized vesicular antigens can be easily recognized and captured by antigen-presenting cells such as dendritic cells, and readily circulated through the lymphatic system, so that they are highly apt to induce immune responses. Representative of nano-sized vesicles are extracellular vesicles (e.g., exosomes, microvesicles, etc.) that spontaneously shed from almost all cell types. Extracellular vesicles range in size from tens to hundreds nm, and consist of a bilayer lipid membrane, with biologically active materials, such as proteins, lipids and genetic materials, contained therein, performing various physiological/pathological functions. Particularly, if originating directly from the plasma membrane of cancer cells, the extracellular vesicles reflect the antigenic content of the cancer cells. Further, cancer cell-derived extracellular vesicles contain high local concentrations of cancer antigens because of their high surface-area-to-volume, and are more apt to induce immunization, compared to an antigen in a receptor form. Moreover, extracellular vesicles may be used as a cell-free vaccine and thus are expected to cause significantly fewer side effects, compared to conventional tumor cell vaccines for which it is difficult to obtain clinical permission.

However, extracellular vesicles are disadvantageous in practical clinical application for the following reasons. A cell line of cancer cells separated directly from patients must be established in order to obtain extracellular vesicles therefrom. It is difficult to secure extracellular vesicles in a large quantity because they are released in a trace amount. Intricate separation and purification of extracellular vesicles requires high expense and much time. Therefore, nanovesicular antigens need to be developed as an alternative to tumor-derived extracellular vesicles.

DISCLOSURE

Technical Problem

The present invention aims to develop a cancer antigen in a nano-sized vesicular form useful for enhancing anticancer immunity and destroying immunological tolerance. Extracellular vesicles spontaneously shed from cancer cells may be useful as a cancer vaccine because they are nano-sized and contain various antigenic proteins identical to those of the cancer cells, but they are difficult to separate on a mass scale and to prepare. It is therefore an object of the present invention to provide a pharmaceutical composition for the treatment of cancer, comprising tumor tissue-derived nanovesicles that retain the advantages of conventional extracellular vesicles and can be prepared at high yield, a method for treating cancer using the same, and a method for preparing the tumor tissue-derived nanovesicles.

However, the objects to be achieved by the present invention are not limited to the foregoing, and the above and other objects, features and other advantages of the present invention will be more clearly understood from the following detailed description.

Technical Solution

In accordance with an aspect thereof, the present invention provides a pharmaceutical composition comprising tumor tissue-derived nanovesicles. In one embodiment of the present invention, the tumor tissue may be a cancer tissue originating from a patient. In another embodiment, the tumor tissue is transformed to express a heat-shock protein. According to a further embodiment, the pharmaceutical composition may further comprise an immune adjuvant, and the adjuvant may be polyI:C. In a still further embodiment, the nanovesicles comprise a component other than that sourced from a plasma membrane of the tumor tissue, and the component may be cyclodextrin or polyethylene glycol. According to sill another embodiment of the present invention, the nanovesicles may have a chemically modified membrane, and the nanovesicles may be chemically modified with a thiol group or an amine group.

In accordance with another aspect thereof, the present invention provides a method for treating cancer, comprising administering a pharmaceutical composition comprising tumor tissue-derived nanovesicles to a subject in need thereof. In this regard, the tumor tissue, the composition, and the nanovesicles are as defined above.

In accordance with a further aspect thereof, the present invention provides a cancer vaccine, comprising tumor tissue-derived nanovesicles as an antigen.

In accordance with a still further aspect thereof, the present invention provides a method for preparing tumor tissue-derived nanovesicles. In one embodiment, the method comprises: separating cells from a tumor tissue; constructing nanovesicles from a suspension of the cells by a process selected from the group consisting of extrusion, sonication, cell lysis, homogenation, freeze-thawing, electroporation, mechanical degradation, and chemical treatment; isolating the constructed nanovesicles from the suspension; and incubating a suspension of the nanovesicles in the presence of an adjuvant.

In another embodiment, the method comprises: separating cells from a tumor tissue; adding an adjuvant to a suspension of the cells to load the adjuvant into the cells; and constructing nanovesicles from the cell suspension by a process selected from the group consisting of extrusion, sonication, cell lysis, homogenation, freeze-thawing, electroporation, mechanical degradation, and chemical treatment.

In another embodiment, the method may further comprise isolating the adjuvant-loaded nanovesicles from the cell suspension.

According to a further embodiment, the isolation may be accomplished using a process selected from the group consisting of density gradient centrifugation, ultracentrifugation, filtration, dialysis, and free-flow electrophoresis.

Advantageous Effects

In spite of reports on using spontaneously shed extracellular vesicles in the development of cancer vaccines, due to their effective anticancer activity, significant limitations have been imposed on the clinical application of the extracellular vesicles because they require in vitro culturing of a patient's cells and are difficult to separate and prepare, in addition to resulting in a low production yield when prepared. In contrast, the tumor tissue-derived nanovesicles according to the present invention can be prepared at high yield while retaining similar properties to those of spontaneously shed extracellular vesicles. Further, the tumor tissue-derived nanovesicles can be diversely modified and can be used as a cancer antigen useful in the development of a cancer vaccine.

BEST MODE

Figure 1:
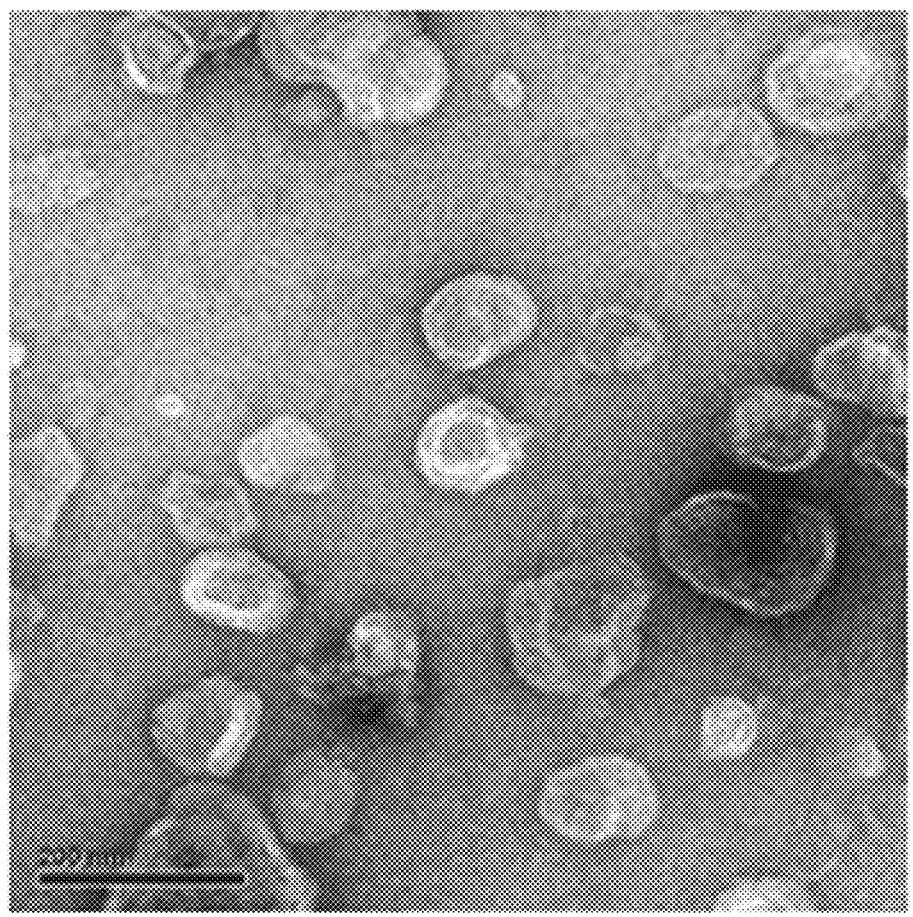
FIG. 1 is a transmission electron microphotograph of the melanoma-derived nanovesicles prepared using sonication.

Leading to the present invention, intensive and thorough research into a cancer vaccine resulted in the finding that nanovesicles originating from tumor tissues evoke anticancer immune activity without inducing immunological tolerance, and can be separated and prepared on a mass scale at high yield.

Extracellular vesicles spontaneously shed from cancer cells are also useful as a cancer vaccine because they reflect the same antigenic content as that which is present in the cancer cells, but they are difficult to separate and prepare on a mass scale.

Culminating in the present invention, the present inventors have undertaken research into a cancer vaccine and found that nanovesicles originating from tumors can be produced on a mass scale without in vitro incubation, and can immunize the cancer patients effectively, when modified, so as to stimulate an immune reaction that could kill the cancer cells.

In detail, the present inventors focused on the development of tumor-derived nanovesicles which can be prepared at high yield while retaining the advantages of conventional extracellular vesicles, and conducted various experiments in which cancer cells were rendered to be rich in antigenic membrane proteins, and prepared into nanovesicles with a size of 100 to 200 nm by sonication or extrusion. The nanovesicles obtained by this method were observed to have similarity to spontaneously shed extracellular vesicles in terms of morphology, size, and density. In addition, when modified by loading an adjuvant thereinto or enriching heat-shock proteins therein, the nanovesicles were found to be improved in anticancer activity.

According to one aspect thereof, the present invention addresses a pharmaceutical composition for the treatment of cancer, comprising tumor tissue-derived nanovesicles. Also, contemplated in accordance with another aspect of the present invention is a cancer vaccine comprising tumor tissue-derived nanovesicles. In the present invention, the tumor tissue includes an autologous cancerous tissue, but is not limited thereto.

In one embodiment of the present invention, the tumor tissue may be melanoma, or colorectal cancer cells. Also, the nanovesicles useful in the present invention may be derived from other cancer cells.

The nanovesicles prepared in the present invention range in size from 50 to 250 nm, and comprise membrane lipids, and antigenic, membrane proteins.

The proteins in the nanovesicles may be analyzed and identified using Western blotting, or other analysis techniques.

As an antigen, the protein of the nanovesicles may include tyrosinase, but is not limited thereto.

For use in stimulating the immune response evoked by the antigen, an adjuvant may be further loaded to the nanovesicles. An example of the adjuvant useful in the present invention is the toll-like receptor 3 ligand, polyI:C, but is not limited thereto, and other toll-like receptor ligands may be employed.

In the present invention, an adjuvant may be combined with nanovesicles to afford adjuvant-loaded nanovesicles, which, however, do not limit the present invention. Various materials stimulatory of immune responses and anticancer effects may be conjugated into the nanovesicles.

The nanovesicles may be enriched with heat-shock protein 90 if they are obtained from tumor cells after the application of thermal stress.

Non-membrane components other than membrane components originating from the tumor tissue may be contained in the nanovesicles of the present invention. Examples of the non-membrane components include cyclodextrin and polyethylene glycol, but are not limited thereto. Also, the membrane components of the nanovesicles may be modified chemically with thiol or amine groups.

The pharmaceutical composition of the present invention may comprise a pharmaceutically acceptable carrier. Examples of the pharmaceutically acceptable carrier include, but are not limited to, physiological saline, polyethylene glycol, ethanol, vegetable oil, and isopropyl myristate.

In accordance with a further aspect thereof, the present invention addresses a method for treating cancer, comprising administering the composition comprising the tumor tissue-derived nanovesicles to a subject in need thereof. As used herein, the term "subject" is intended to refer to targets that need the treatment of a disease, and more particularly, means humans and non-human mammals such as primates, mice, rats, dogs, cats, horses, cattles, and the like. It will be appreciated by those skilled in the art that "pharmaceutically effective amount" may be determined in consideration of various factors including the patient's age, weight, age, gender, general health, gender and diet, the time of administration, the route of administration, the rate of excretion, and the severity of diseases.

The effective dosage of the composition in accordance with the present invention depends on various factors, including the patient' condition and weight, the severity of disease, drug formulations, the route of administration, and the time of administration. In general, the composition of the present invention may be administered in a single dose, and preferably in multiple doses per day at a daily dose ranging from 0.001 to 100 mg/kg, and preferably from 0.01 to 30 mg/kg. The pharmaceutical composition of the present invention may be administered through various routes into mammals such as mice, rats, livestock, humans, etc. No limitations are imposed on the method of administration. For example, it may administer orally, rectally or by intravenous, intramuscular, subcutaneous, intradural, or intracerebroventricular injection.

In accordance with a still further aspect thereof, the present invention addresses a method for preparing tumor tissue-derived nanovesicles. In one embodiment of this aspect, the nanovesicles may be modified by loading an adjuvant thereto or enriching heat-shock proteins therein so as to evoke stronger immune responses.

The nanovesicles which act as an immunogen in the cancer vaccine of the present invention may be prepared from plasma membranes of cancer tissues by sonication or extrusion. Below, a detailed description is given of the preparation of tumor tissue-derived nanovesicles.

In one embodiment of the present invention, the method for preparing tumor tissue-derived nanovesicles comprises (a) separating cells from a tumor tissue; (b) constructing nanovesicles from a suspension of the cells by a process selected from the group consisting of extrusion, sonication, cell lysis, homogenation, freeze-thawing, electroporation, mechanical degradation, and chemical treatment; (c) isolating the constructed nanovesicles from the suspension; and (d) incubating a suspension of the nanovesicles in the presence of an adjuvant.

According to another embodiment of the present invention, the method for preparing tumor tissue-derived nanovesicles comprises (a) separating cells from a tumor tissue; (b) adding an adjuvant to a suspension of the cells so as to load the adjuvant into the cells; and (c) constructing nanovesicles from the cell suspension by a process selected from the group consisting of extrusion, sonication, cell lysis, homogenation, freeze-thawing, electroporation, mechanical degradation, and chemical treatment.

In a further embodiment of the present invention, the method may further comprise isolating the adjuvant-loaded nanovesicles from the cell suspension. In this context, the isolation may be accomplished using a process selected from the group consisting of density gradient centrifugation, ultracentrifugation, filtration, dialysis, and free-flow electrophoresis.

A better understanding of the present invention may be obtained through the following examples which are set forth to illustrate, but are not to be construed as limiting the present invention.

EXAMPLES

Example 1

Figure 2:
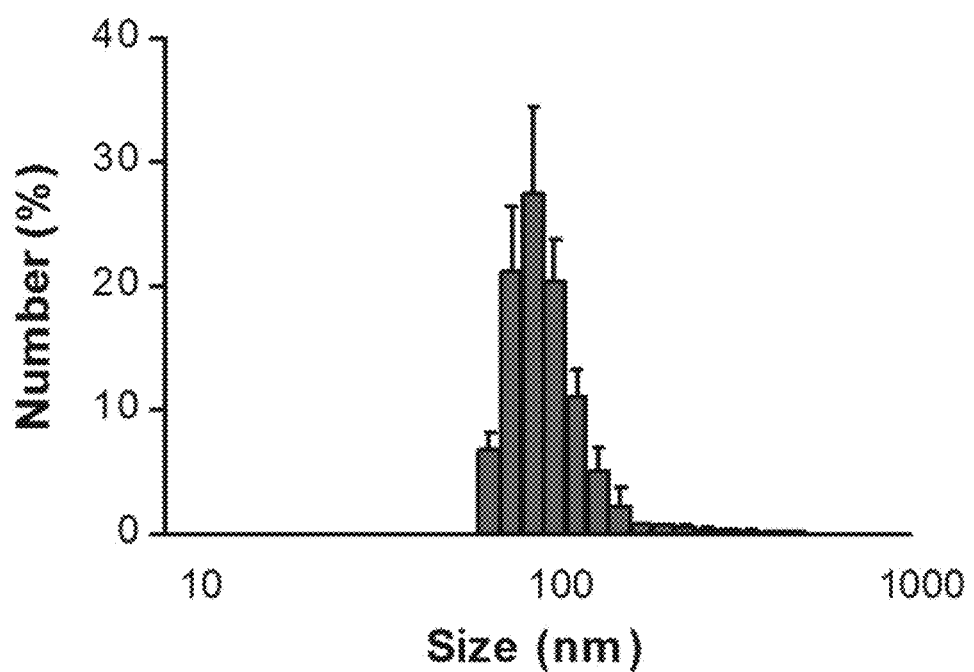
FIG. 2 is a graph of particle sizes of the melanoma-derived nanovesicles prepared using sonication, as measured by a dynamic light scattering-based particle size analyzer.

Preparation of Nanovesicles from Melanoma Cells Using Sonication and Their Characterization The melanoma cell line (B16BL6) was subcutaneously injected into mice (C57/BL6, female), cultured for 2~3 weeks to a mass size of 1.0~1.5 cm, and then tumor tissues were obtained by surgical excision. The melanoma tissue was ground and passed through a 45 μm filter for homogenization, followed by incubation at 4° C. for 30 min in a hypotonic solution. Then, the filtrate was homogenized with 100 strokes of a homogenizer and the homogenate was adjusted to have a final salt concentration of 150 mM to form vesicles. Centrifugation at 500×g for 10 min removed nucleoproteins and intact cells as a pellet, and the supernatant was sonicated for 30 min in a water bath sonicator to form nano-sized vesicles which were constant in size. Subsequently, cell debris and mitochondria were removed by centrifugation at 10,000×g for 20 min. After being collected, the supernatant was adjusted into a volume of 10 ml, placed on a sucrose cushion comprising 0.1 ml of 2.0 M sucrose as a lower layer and 0.35 ml of 0.8 M sucrose as an upper layer in an ultracentrifuge tube, and ultracentrifuged at 100,000×g for 2 hrs. The sucrose layer into which the vesicles were submerged was separated, mixed with 4.8 ml of 30% Optiprep, and overlaid with 3.0 ml of 20% Optiprep and 2.5 ml of 5% Optiprep in the order before ultracentrifugation at 200,000×g for 2 hrs. At last, a layer of nanovesicles was formed between the 5% and the 20% Optiprep. FIG. 1 is a transmission electron microphotograph of the melanoma-derived nanovesicles prepared in Example 1. As can be seen in the TEM image of FIG. 1, the nanovesicles were composed of a lipid bilayer with a globular shape. FIG. 2 is a graph of particle sizes of the nanovesicles as measured by a dynamic light scattering-based particle size analyzer. As is understood from the data of FIG. 2, the nanovesicles had a mean size of 101.6±24.8 nm.

Figure 3:
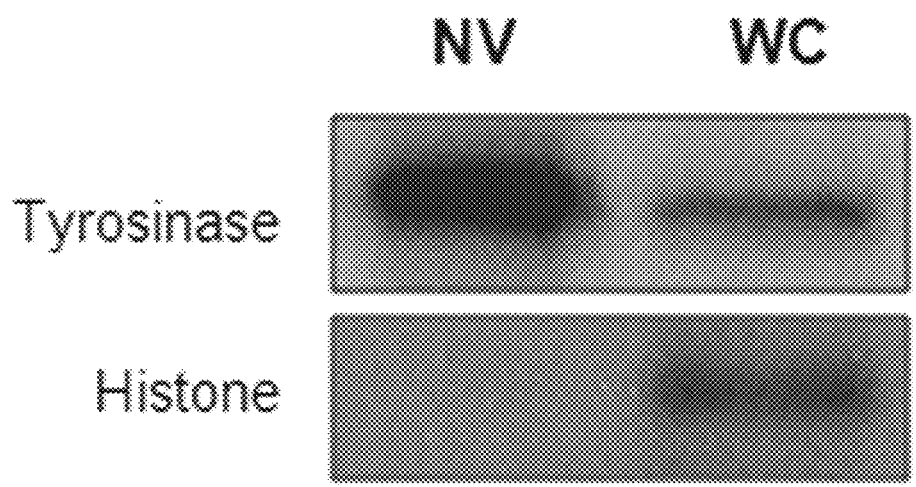
FIG. 3 shows Western blots of the antigenic membrane protein tyrosinase and the nucleoprotein histone which become enriched and sparse, respectively, in the nanovesicles prepared using sonication.

FIG. 3 shows Western blots of the membrane protein tyrosinase and the nucleoprotein histone, each present in 10 μg of the proteins prepared from the nanovesicles and the cancer cells (WC). The nanovesicles were observed to contain the membrane antigenic protein tyrosinase in a higher concentration, but not the nucleoprotein histone in a lower concentration, compared to the melanoma cells from which the nanovesicles were derived.

Example 2

Figure 4:
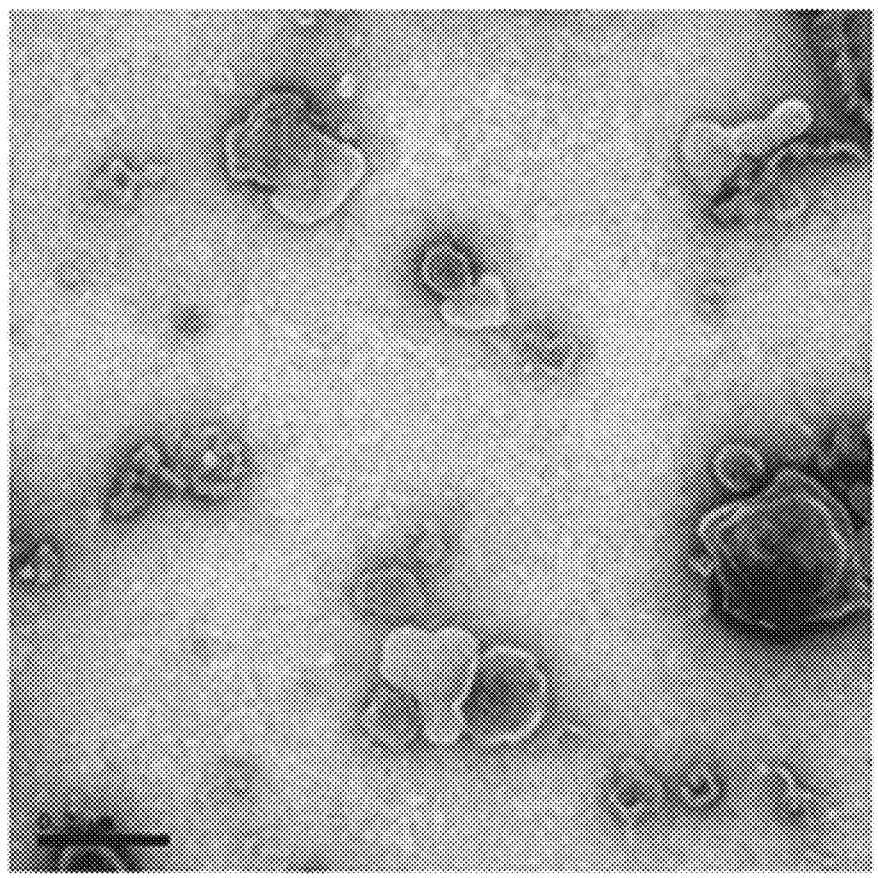
FIG. 4 is a transmission electron microphotograph of the colorectal cancer cell-derived nanovesicles prepared using sonication.

Preparation of Nanovesicles from Colorectal Cancer Cells Using Sonication and Their Characterization The colorectal cell line (Colon26) was subcutaneously injected into mice (BALB/C, female), cultured for 2~3 weeks to a mass size of 1.0~1.5 cm, and then tumor tissues were obtained by surgical excision. The same procedure as in Example 1 was repeated. That is, the colorectal cancer tissue was ground and filtered for homogenization, followed by incubation at 4° C. for 30 min in a hypotonic solution. Then, the filtrate was homogenized with 100 strokes of a homogenizer and the homogenate was adjusted to have a final salt concentration of 150 mM to form vesicles. Centrifugation at 500×g for 10 min removed nucleoproteins and intact cells as a pellet, and the supernatant was sonicated for 30 min in a water bath sonicator to form nano-sized vesicles which were constant in size. Subsequently, cell debris and mitochondria were removed by centrifugation at 10,000×g for 20 min. After being collected, the supernatant was adjusted into a volume of 10 ml, placed on a sucrose cushion comprising 0.1 ml of 2.0 M sucrose as a lower layer and 0.35 ml of 0.8 M sucrose as an upper layer in an ultracentrifuge tube, and ultracentrifuged at 100,000×g for 2 hrs. The sucrose layer into which the vesicles were submerged was, in the following order, separated, mixed with 4.8 ml of 30% Optiprep, and overlaid with 3.0 ml of 20% Optiprep and 2.5 ml of 5% Optiprep, before ultracentrifugation at 200,000×g for 2 hrs. Finally, a layer of nanovesicles was formed between the 5% and the 20% Optiprep. FIG. 4 is a transmission electron microphotograph of the colorectal cancer cell-derived nanovesicles prepared in this manner.

Example 3

Figure 5:
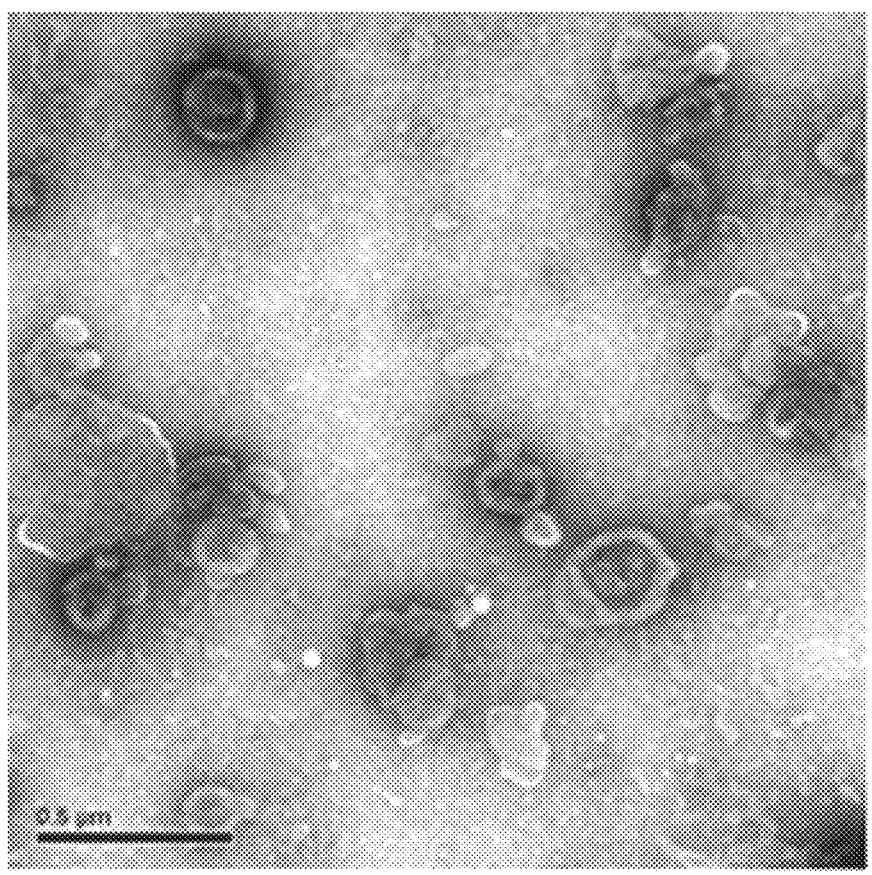
FIG. 5 is a transmission electron microphotograph of the melanoma-derived nanovesicles prepared using extrusion.

Preparation of Nanovesicles from Melanoma Cells Using Extrusion and Their Characterization The melanoma cell line (B16BL6) was subcutaneously injected into mice (C57/BL6, female), cultured for 2~3 weeks to a mass size of 1.0~1.5 cm, and then tumor tissues were obtained by surgical excision. The melanoma tissue was ground and passed through a 45 μm filter for homogenization, followed by incubation at 4° C. for 30 min in a hypotonic solution. Then, the filtrate was homogenized with 100 strokes of a homogenizer and the homogenate was adjusted to have a final salt concentration of 150 mM to form vesicles. Centrifugation at 500×g for 10 min removed nucleoproteins and intact cells as a pellet, and the supernatant was rendered to pass three times through a membrane filter with a pore size of 1 μm and then three times through a membrane filter with a pore size of 0.4 μm. After being collected, the filtrate was adjusted into a volume of 10 ml, placed on a sucrose cushion comprising 0.1 ml of 2.0 M sucrose as a lower layer and 0.35 ml of 0.8 M sucrose as an upper layer in an ultracentrifuge tube, and ultracentrifuged at 100,000×g for 2 hrs. The sucrose layer into which the vesicles were submerged was, in the following order, separated, mixed with 4.8 ml of 30% Optiprep, and overlaid with 3.0 ml of 20% Optiprep and 2.5 ml of 5% Optiprep, before ultracentrifugation at 200,000×g for 2 hrs. Finally, a layer of nanovesicles was formed between the 5% and the 20% Optiprep. FIG. 5 is a transmission electron microphotograph of the melanoma-derived nanovesicles prepared in this manner.

Example 4

Immune Response of Dendritic Cells Induced by Melanoma-Derived Nanovesicles

Bone marrow cells were harvested from the femur and the tibia of mice (C57/BL6, female). After erythrolysis, the bone marrow cells were differentiated into dendritic cells in 10% FBS/RPMI supplemented with nutrients and 20 ng/ml GM- CSF for one week. Separately, the nanovesicles prepared in Example 1 were labeled with DiI, a lipophilic, red fluorescent dye. The dendritic cells were incubated with the nanovesicles and examined for endocytosis using FACS.

Figure 6:
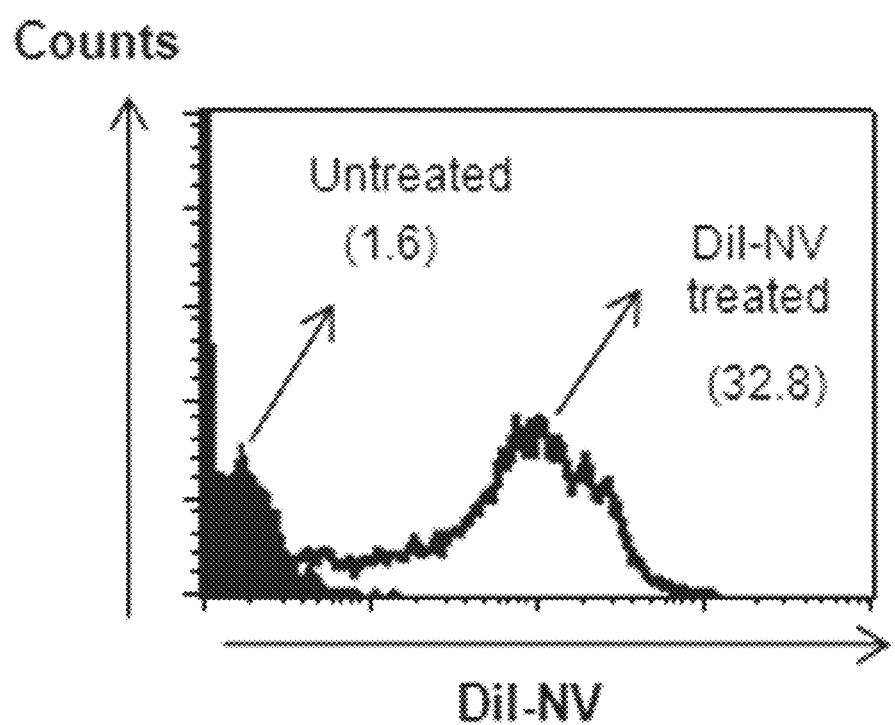
FIG. 6 is a flow cytogram showing the recognition and endocytosis of the DiI-labeled nanovesicles by bone marrow-derived dendritic cells.

FIG. 6 is a flow cytogram showing the endocytosis of the nanovesicles by dendritic cells wherein numerals within parentheses represent MFI (mean fluorescence intensity) values. Differentiated dendritic cells were seeded at a density of $1\times10^5$ cells/well into 24-well plates, and treated with 0, 0.1, 1.0, 2.0, or 10.0 μg/ml of the nanovesicles for 24 hrs. The cell cultures were harvested and centrifuged at 500×g at 4° C. for 10 min, and the supernatant was again centrifuged at 3000×g for 20 min. The resulting supernatant was quantitatively analyzed for cytokine using ELISA (enzyme linked immunosorbent assay).

Figure 7:
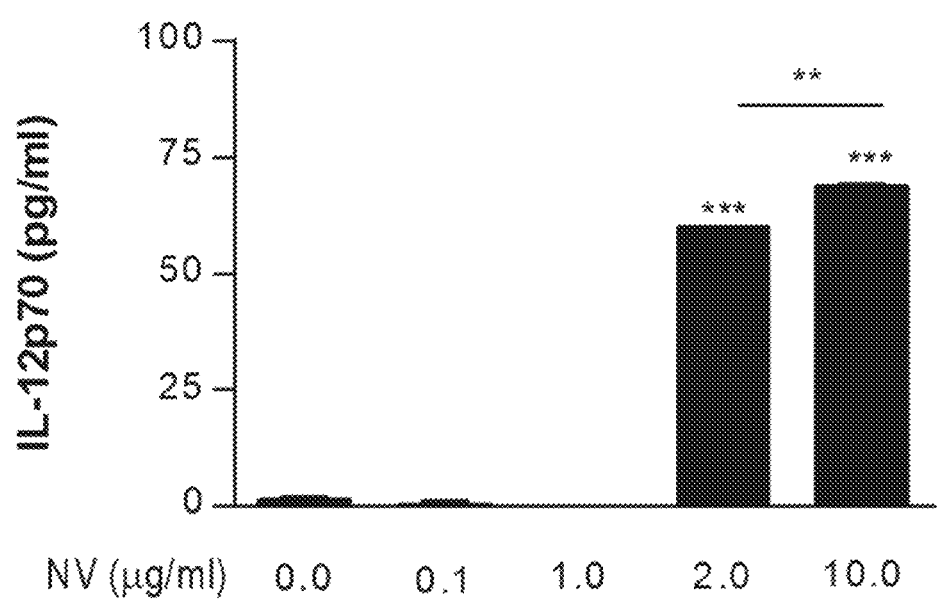
FIG. 7 is a graph of cytokine levels in dendritic cells showing that the cytokine IL-12p70 is increased in level in a manner dependent on the dose of the melanoma-derived nanovesicles.

FIG. 7 is a graph of cytokine levels showing that IL-12p70, a cytokine inducing T helper type 1 response, is increased in level in a manner dependent on the dose of the nanovesicles. These data are indicative of the fact that the melanoma-derived nanovesicles act like antigen-presenting cells such as dendritic cells, giving rise to an anticancer effect.

Example 5

Assay for Inhibitory Activity of Melanoma-Derived Nanovesicles against Cancer Growth Each mouse (C57/BL6, female) was subcutaneously injected with $5\times10^5$ melanoma cells (B16BL6), and bred for one week so as to form a measurable mass of cancer. Then, the melanoma-derived nanovesicles prepared in the same manner as in Example 1 were intraperitoneally injected three times at a dose of 10 μg alone or in combination with 50 μg of the adjuvant polyI:C to the mice at regular intervals of one week. The size of the cancer mass was measured two or three times a week. The volume of cancer mass was calculated according to the formula $v=l\times s^2/2$ wherein v represents volume, l is a length of the longest axis of the cancer mass, and s is a length of the axis perpendicular to the longest axis.

Figure 8:
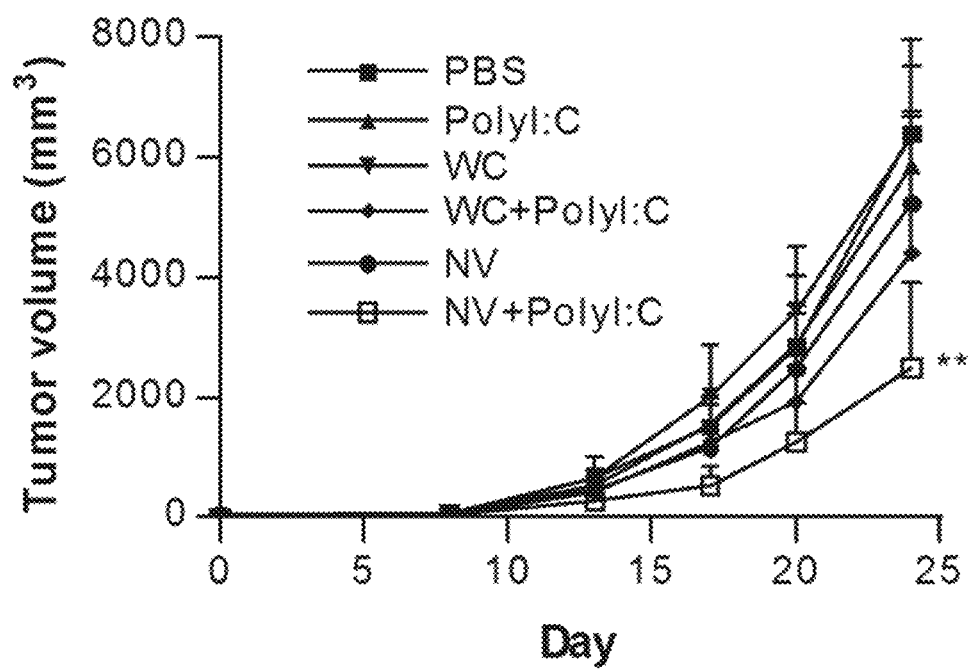
FIG. 8 is a graph in which tumor volumes in mice treated with or without the melanoma-derived nanovesicles and/or an adjuvant are plotted against time, demonstrating the efficacy of the melanoma-derived nanovesicles in combination with the adjuvant as a cancer vaccine.

FIG. 8 is a graph in which tumor volumes in mice treated with or without the nanovesicles and/or the adjuvant are plotted against time, demonstrating the efficacy of the melanoma-derived nanovesicles in combination with the adjuvant as a cancer vaccine. As can be seen in FIG. 8, a combination of the nanovesicles and the adjuvant acted as a vaccine to decrease the growth of cancer. Also, the adjuvant-loaded nanovesicles of the present invention was proven to effectively inhibit the growth of cancer, as analyzed by the formula T/C ratio (=[(median tumor volume of treated group)/(median tumor volume of control group)×100], which was calculated to be 34% for the adjuvant-loaded nanovesicles, in light of the critical value of 42%. Particularly, compared to cancer cells themselves (WC), the nanovesicles were highly inhibitory of the growth of cancer. Therefore, the tumor-derived nanovesicles were identified as being effective as a cancer vaccine.

Example 6

Assay for Inhibitory Activity of Melanoma-Derived Nanovesicles against Cancer Metastasis Each mouse (C57/BL6, female) was intravenously injected with $1\times10^5$ melanoma cells (B16BL6) so as to form tumor in the lung. Four days later, 10 μg of the melanoma-derived nanovesicles prepared in the same manner as in Example 1 was intraperitoneally injected alone or in combination with 50 μg of polyI:C three times at regular intervals of four days to the mice. On day 14, the mice were euthanized and the lungs were excised.

Figure 9:
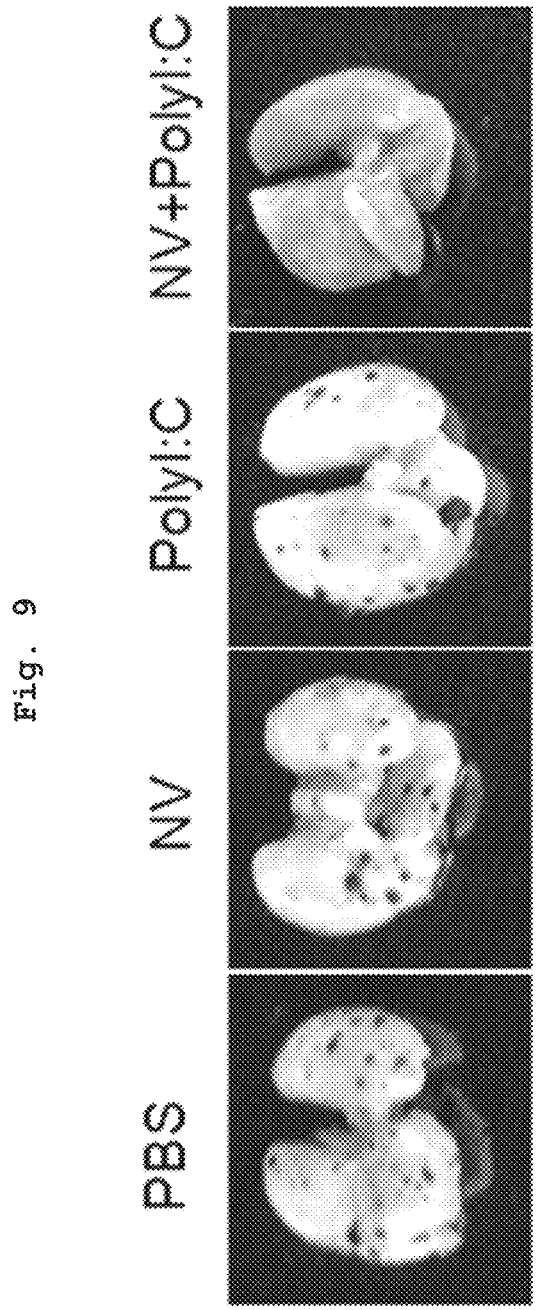
FIG. 9 shows images of the lungs excised from mice immunized with or without the melanoma-derived nanovesicles and/or an adjuvant after the metastasis of melanoma cells thereto.

FIG. 9 shows images of the lungs excised from mice immunized with or without the melanoma-derived nanovesicles and/or the adjuvant after the metastasis of melanoma cells thereto. As can be seen, a combination of the nanovesicles and the adjuvant effectively acted as a cancer vaccine to elicit immunity to the metastasis of melanoma cells to the lungs. In the images, tumor masses of melanoma are represented as black spots.

Figure 10:
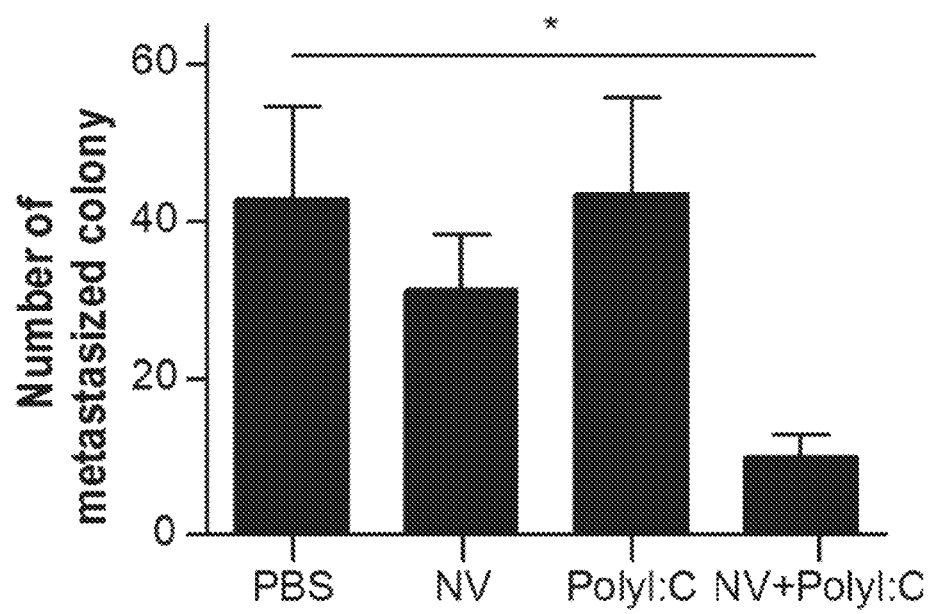
FIG. 10 is a graph of the number of metastasized colonies in mouse lungs.

The metastasized colonies were counted, and the results are shown in FIG. 10. As can be seen in FIG. 10, a significantly lower number of metastasized colonies were detected in the lungs treated with a combination of the nanovesicles and the adjuvant.

Figure 11:
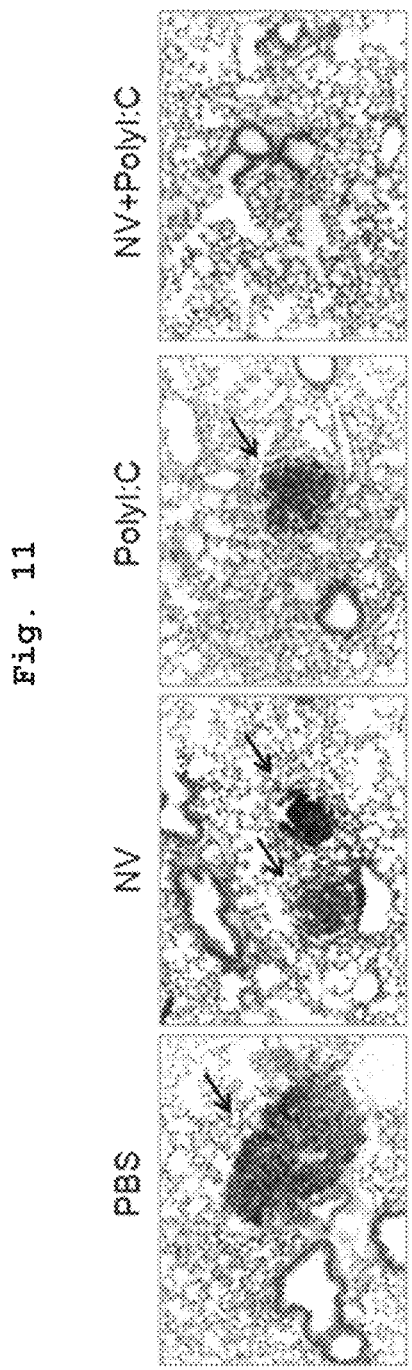
FIG. 11 shows images of the lungs stained with H & E after treatment with or without the melanoma-derived nanovesicles and/or the adjuvant.

The excised lungs were sectioned, and stained with H & E (Hematoxylin-Eosin) to color nuclei of cells blue, and the cytoplasm red. FIG. 11 shows images of the lungs stained with H & E after treatment with or without the nanovesicles and/or the adjuvant. As can be seen, only a combination of the nanovesicles and the adjuvant reduced the metastasis of melanoma (indicated by arrows), demonstrating that the tumor-derived nanovesicles can be used as a cancer vaccine which elicits significant immunity against cancer metastasis.

Example 7

Induction of Immune Response of Dendritic Cells by Colorectal Cancer Cell-Derived Nanovesicles Bone marrow cells were harvested from the femur and the tibia of mice (BALB/C, female). After erythrolysis, the bone marrow cells were differentiated into dendritic cells in 10% FBS/RPMI supplemented with nutrients and 20 ng/ml GM-CSF for one week. Differentiated dendritic cells were seeded at a density of $1\times10^5$ cells/well into 24-well plates, and treated for 24 hrs with 10.0 μg/ml of the colorectal cancer-derived nanovesicles prepared in Example 2. The cell cultures were harvested and centrifuged at 500×g at 4° C. for 10 min, and the supernatant was again centrifuged at 3000×g for 20 min. The resulting supernatant was quantitatively analyzed for cytokine using ELISA (enzyme linked immunosorbent assay).

Figure 12:
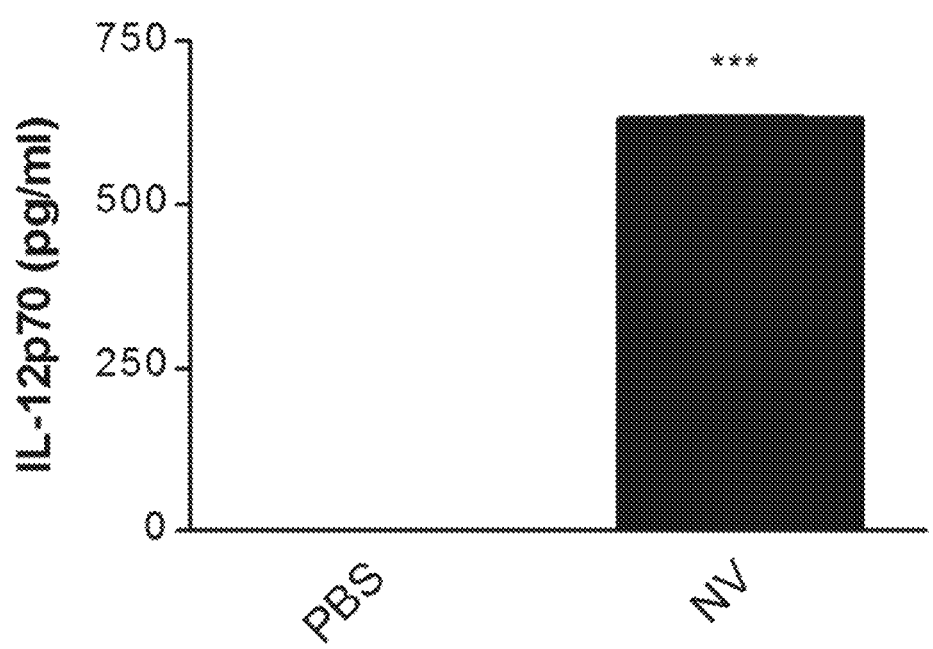
FIG. 12 is a graph of cytokine levels showing that the level of the cytokine IL-12p70 is increased with an increase in the dose of the colorectal cancer-derived nanovesicles, as analyzed by ELISA.

FIG. 12 is a graph of cytokine levels showing that the level of IL-12p70, a cytokine inducing T helper type 1 response, is increased with an increase in the dose of the nanovesicles. These data are indicative of the fact that the colorectal cancer-derived nanovesicles act like antigen-presenting cells such as dendritic cells, giving rise to an anticancer effect.

Example 8

Assay for Inhibitory Activity of Colorectal Cancer-Derived Nanovesicles against Cancer Growth Each mouse (BALB/C, female) was subcutaneously injected with $5\times10^5$ colorectal cancer cells (Colon26), and bred for one week so as to form a measurable mass of cancer. Then, the colorectal cancer-derived nanovesicles prepared in the same manner as in Example 2 were intraperitoneally injected three times at a dose of 10 μg alone or in combination with 50 μg of the adjuvant polyI:C to the mice at regular intervals of one week. The size of the cancer mass was measured two or three times a week. The volume of tumor mass was calculated according to the formula $v=l\times s^2/2$ wherein v represents volume, l is a length of the longest axis of the cancer mass, and s is a length of the axis perpendicular to the longest axis.

Figure 13:
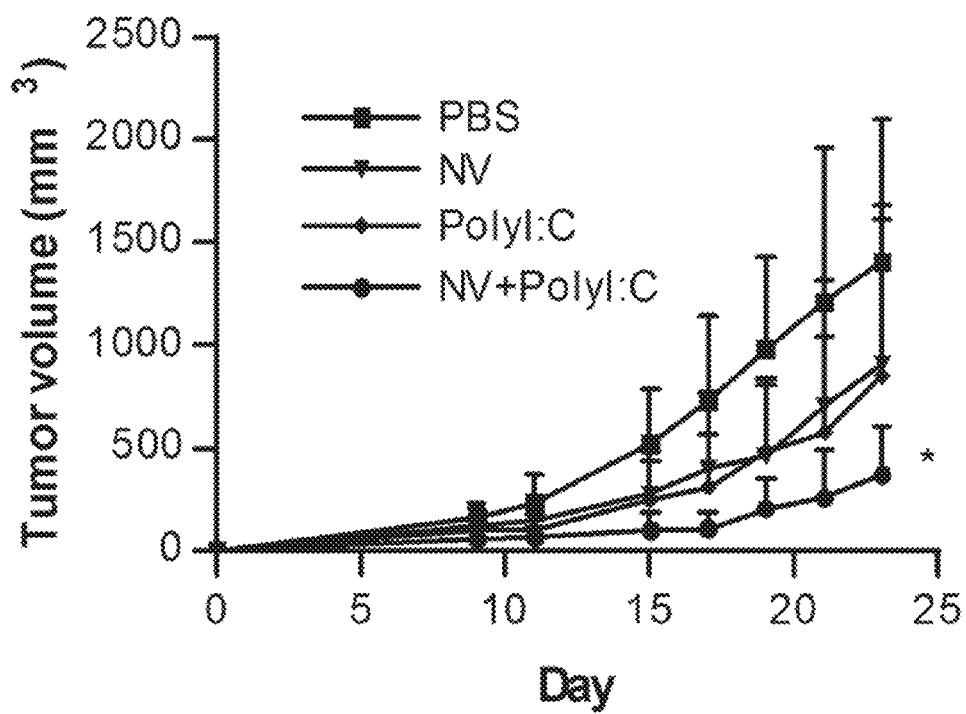
FIG. 13 is a graph in which tumor volumes in mice treated with or without the colorectal cancer-derived nanovesicles and/or the adjuvant are plotted against time, demonstrating the efficacy of the colorectal cancer-derived nanovesicles in combination with the adjuvant as a cancer vaccine.

FIG. 13 is a graph in which tumor volumes in mice treated with or without the nanovesicles and/or the adjuvant are plotted against time, demonstrating the efficacy of the colorectal cancer-derived nanovesicles in combination with the adjuvant as a cancer vaccine. As can be seen in FIG. 13, a combination of the nanovesicles and the adjuvant acted as a vaccine to significantly decrease the growth of cancer. Also, a combination of the nanovesicles and the adjuvant in accordance with the present invention was proven to effectively inhibit the growth of cancer, as analyzed in light of T/C ratio, which was calculated to be 27% for the adjuvant-loaded nanovesicles. Therefore, nanovesicles, if derived from cancer cells, irrespective of the type of cancer, can be used as a cancer antigen to elicit immunity to the cancer.

Example 9

Preparation of Adjuvant-Loaded Nanovesicles

A tumor tissue obtained from mice was ground, and passed through a 45 μm filter for homogenization, followed by incubation at 4° C. for 30 min in a hypotonic solution and then for an additional 10 min with 1 mg/ml of the adjuvant polyI:C. Subsequently, the filtrate was homogenized with 100 strokes of a homogenizer and the homogenate was adjusted to have a final salt concentration of 150 mM to form vesicles. Centrifugation at 500×g for 10 min removed nucleoproteins and intact cells as a pellet, and the supernatant was rendered to pass three times through a membrane filter with a pore size of 1 μm and then three times through a membrane filter with a pore size of 0.4 μm. After being collected, the filtrate was adjusted into a volume of 10 ml, placed on a sucrose cushion comprising 0.1 ml of 2.0 M sucrose as a lower layer and 0.35 ml of 0.8 M sucrose as an upper layer in an ultracentrifuge tube, and ultracentrifuged at 100,000×g for 2 hrs. The sucrose layer into which the vesicles were submerged was, in the following order, separated, mixed with 4.8 ml of 30% Optiprep, and overlaid with 3.0 ml of 20% Optiprep and 2.5 ml of 5% Optiprep, before ultracentrifugation at 200,000×g for 2 hrs. Finally, a layer of nanovesicles was formed between the 5% and the 20% Optiprep.

Figure 14:
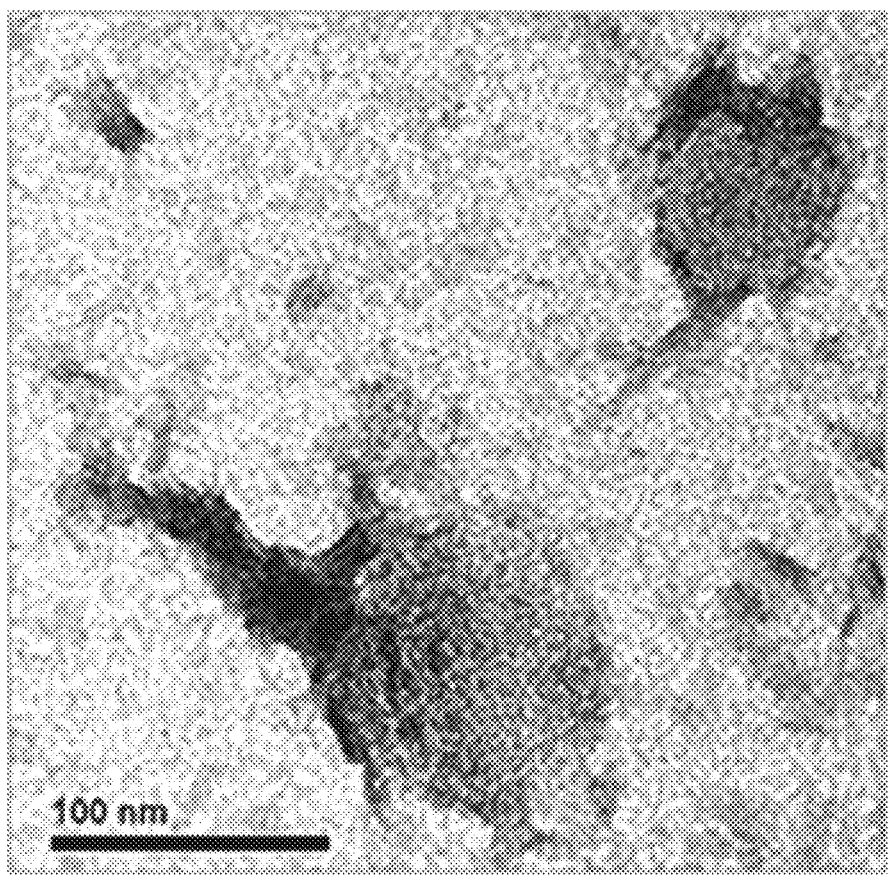
FIG. 14 is a transmission electron microphotograph of the melanoma-derived nanovesicles loaded with the adjuvant polyI:C.

FIG. 14 is a transmission electron microphotograph of the melanoma-derived nanovesicles prepared in this manner, showing the conjugation of the dsRNA polyI:C into the nanovesicles.

Example 10

Assay for Inhibitory Activity of Adjuvant-Loaded Nanovesicles against Cancer Growth Each mouse (C57/BL6, female) was subcutaneously injected with 5×10$^5$ melanoma cells (B16BL6), and bred for one week so as to form a measurable mass of cancer. Then, 10 μg of the polyI:C-loaded, melanoma-derived nanovesicles prepared in the same manner as in Example 9 were intraperitoneally injected three times at to the mice at regular intervals of one week. The size of the cancer mass was measured two or three times a week. The volume of cancer mass was calculated according to the formula v=l×s$^2$/2 wherein v represents volume, l is a length of the longest axis of the cancer mass, and s is a length of the axis perpendicular to the longest axis.

Figure 15:
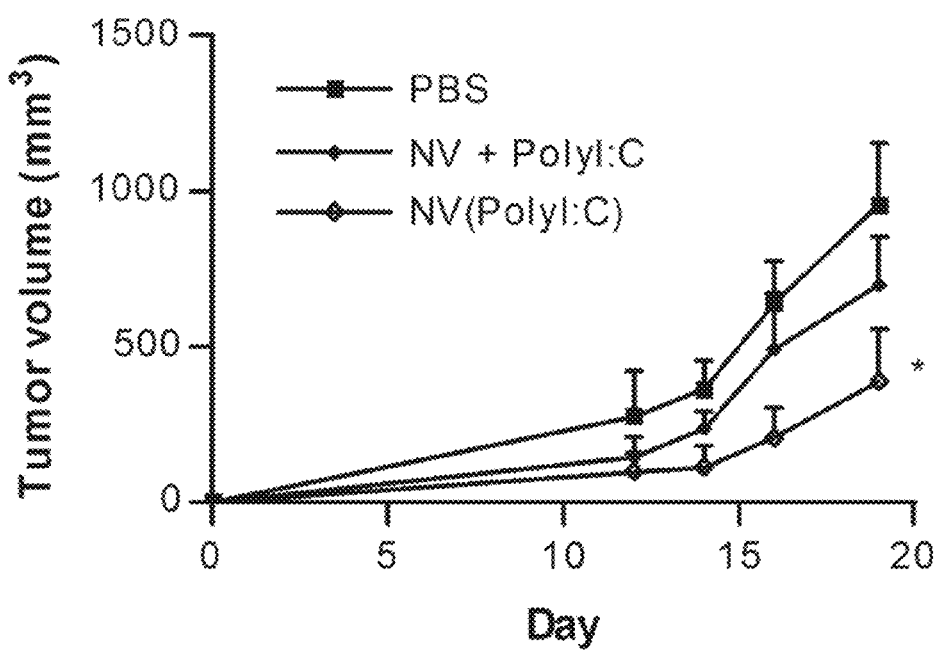
FIG. 15 is a graph in which tumor volumes in mice treated with or without the melanoma-derived nanovesicles and/or the adjuvant are plotted against time, demonstrating the efficacy of the melanoma-derived nanovesicles in combination with the adjuvant as a cancer vaccine.

As shown in FIG. 15, higher anticancer activity was obtained when 10 μg of the adjuvant-loaded nanovesicles ([NV(PolyI:C)]) was used, compared to a combination of 10 μg of the nanovesicles and 50 μg of the adjuvant ([NV+PolyI:C]). The adjuvant-loaded nanovesicles were also proven to have effective anticancer activity as its T/C ratio was calculated to be 33%. These data indicate that when loaded into the nanovesicles, the adjuvant is not diffused, but increases in local acting concentration, and particularly demonstrate that toll-like receptor 3, activated by polyI:C, is present in endosomes of immune cells and can be delivered by means of nanovesicles.

Example 11

Preparation of Heat-Shock Protein-Enriched Nanovesicles

Tumor tissues from mice were incubated for 1.5 hrs under a heat stress of 42° C. in 10% FBS/MEM. Then, the tumor tissues were ground and passed through a 45 μm filter for homogenization, followed by incubation at 4° C. for 30 min in a hypotonic solution. Then, the filtrate was homogenized with 100 strokes of a homogenizer and the homogenate was adjusted to have a final salt concentration of 150 mM to form vesicles. Centrifugation at 500×g for 10 min removed nucleoproteins and intact cells as a pellet, and the supernatant was sonicated for 30 min in a water bath sonicator to form nano-sized vesicles which were constant in size. Subsequently, cell debris and mitochondria were removed by centrifugation at 10,000×g for 20 min. After being collected, the supernatant was adjusted into a volume of 10 ml, placed on a sucrose cushion comprising 0.1 ml of 2.0 M sucrose as a lower layer and 0.35 ml of 0.8 M sucrose as an upper layer in an ultracentrifuge tube, and ultracentrifuged at 100,000×g for 2 hrs. The sucrose layer into which the vesicles were submerged was, in the following order, separated, mixed with 4.8 ml of 30% Optiprep, and overlaid with 3.0 ml of 20% Optiprep and 2.5 ml of 5% Optiprep, before ultracentrifugation at 200,000×g for 2 hrs. At last, a layer of nanovesicles was formed between the 5% and the 20% Optiprep.

Figure 16:
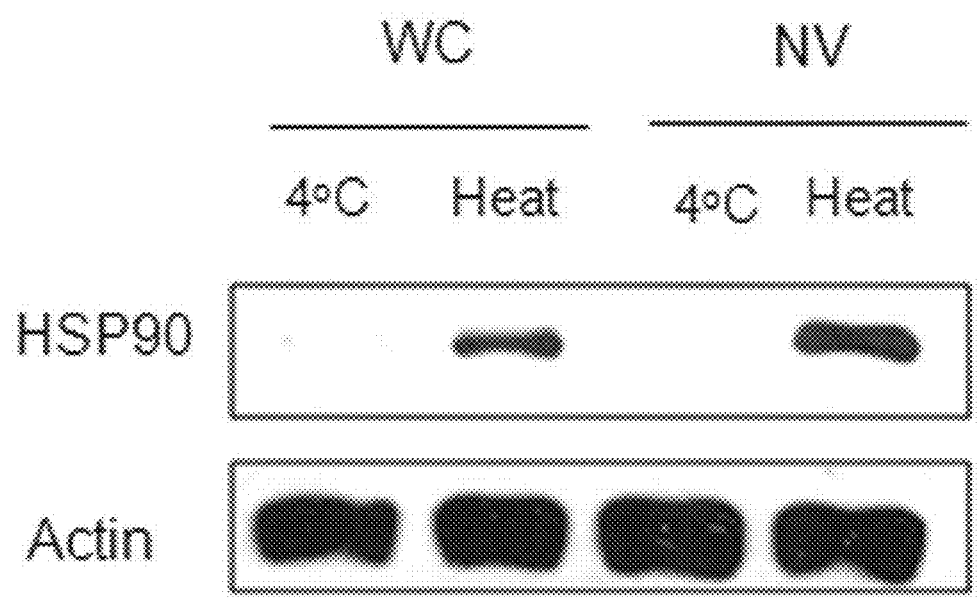
FIG. 16 shows Western blots of a heat-shock protein, showing that heat-shock protein-enriched nanovesicles can be derived from melanoma after incubation under a thermal stress.

FIG. 16 shows Western blots of heat-shock protein 90 (HSP90) from nanovesicles derived from melanoma after incubation under a thermal stress of 42° C. As can be seen in FIG. 16, a thermal stress of 42° C. increased the expression level of heat-shock protein 90 (HSP90). Particularly, the heat-shock protein was 1.8-fold enriched in the nanovesicles, compared to cancer cells themselves. When applied to cancer patients, the heat-shock protein-enriched nanovesicles are expected to elicit more potent anticancer activity as the heat-shock protein acts immunogenically to evoke immunity to the heat shock protein involved in oncogenesis.

These and other changes can be made to the invention in light of the above detailed description. In general, the terms used in the following claims should not be construed to limit the invention to the specific embodiments disclosed in the specification, unless the above detailed description explicitly defines such terms. Accordingly, the actual scope of the invention encompasses the disclosed embodiments and all equivalent ways of practicing or implementing the invention under the claims.

INDUSTRIAL APPLICABILITY

As described hitherto, the tumor tissue-derived nanovesicles according to the present invention can be prepared at high yield while retaining similar properties to those of spontaneously shed extracellular vesicles. In addition, the tumor tissue-derived nanovesicles can be diversely modified and can be used as a cancer antigen useful in the development of a cancer vaccine.

The invention claimed is:

1. A pharmaceutical composition for treatment of cancer, comprising nanovesicles derived from a tumor tissue,
wherein
the nanovesicles are prepared by a method comprising:
(a) separating cells from a tumor tissue;
(b) constructing nanovesicles from a suspension of the cells by a process selected from the group consisting of extrusion, sonication, cell lysis, homogenation, freeze-thawing, electroporation, mechanical degradation, and chemical treatment;
(c) isolating the constructed nanovesicles from the suspension; and
(d) incubating a suspension of the nanovesicles in presence of an adjuvant,
or by a method comprising:
(e) separating cells from a tumor tissue;
(f) adding an adjuvant to a suspension of the cells to load the adjuvant into the cells; and
(g) constructing nanovesicles from the cell suspension by a process selected from the group consisting of extrusion, sonication, cell lysis, homogenation, freeze-thawing, electroporation, mechanical degradation, and chemical treatment.

2. The pharmaceutical composition of claim 1, wherein the tumor tissue is transformed to express a heat-shock protein.

3. The pharmaceutical composition of claim 1, further comprising an immune adjuvant.

4. The pharmaceutical composition of claim 3, wherein the immune adjuvant is polyI:C.

5. The pharmaceutical composition of claim 1, wherein the nanovesicles comprise a component other than that sourced from a plasma membrane of the tumor tissue.

6. The pharmaceutical composition of claim 5, wherein the component is cyclodextrin or polyethylene glycol.

7. The pharmaceutical composition of claim 1, wherein the nanovesicles have a chemically modified membrane.

8. The pharmaceutical composition of claim 7, wherein the nanovesicles are chemically modified with a thiol group or an amine group.

9. A method for treating cancer, comprising administering a pharmaceutical composition comprising tumor tissue-derived nanovesicles of claim 1 to a subject in need thereof.

10. The method of claim 9, wherein the tumor tissue is transformed to express a heat shock protein.

11. The method of claim 9, wherein the pharmaceutical composition further comprises an immune adjuvant.

12. The method of claim 11, wherein the immune adjuvant is polyI:C.

13. The method of claim 9, wherein the nanovesicles comprise a component other than that sourced from a plasma membrane of the tumor tissue.

14. The method of claim 13, wherein the component is cyclodextrin or polyethylene glycol.

15. The method of claim 9, wherein the nanovesicles have a chemically modified membrane.

16. The method of claim 15, wherein the nanovesicles are chemically modified with a thiol group or an amine group.

17. A method for preparing tumor tissue-derived nanovesicles, comprising:
(a) separating cells from a tumor tissue;
(b) constructing nanovesicles from a suspension of the cells by a process selected from the group consisting of extrusion, sonication, cell lysis, homogenation, freeze-thawing, electroporation, mechanical degradation, and chemical treatment;
(c) isolating the constructed nanovesicles from the suspension; and
(d) incubating a suspension of the nanovesicles in presence of an adjuvant.

18. A method for preparing tumor tissue-derived nanovesicles, comprising:
(a) separating cells from a tumor tissue;
(b) adding an adjuvant to a suspension of the cells to load the adjuvant into the cells; and
(c) constructing nanovesicles from the cell suspension by a process selected from the group consisting of extrusion, sonication, cell lysis, homogenation, freeze-thawing, electroporation, mechanical degradation, and chemical treatment.

19. A cancer vaccine, comprising tumor tissue-derived nanovesicles of claim 1 as an antigen.

* * * * *